United States Patent [19]

Scolastico et al.

[11] 4,439,366
[45] Mar. 27, 1984

[54] DERIVATIVES OF CHENODEOXYCHOLIC ACID

[76] Inventors: Carlo Scolastico, Vallisneri St., 13 B-Milan; Cesare Sirtori, Bossi St., 1 Milan, both of Italy; David Kritchevsky, 36 St. at Spruce, Philadelphia, Pa. 19105

[21] Appl. No.: 392,891

[22] Filed: Jun. 28, 1982

[30] Foreign Application Priority Data

Jul. 24, 1981 [IT] Italy .................... 23109 A/81

[51] Int. Cl.$^3$ .............................. C07J 13/00
[52] U.S. Cl. ................................. 260/397.1
[58] Field of Search ..................... 260/397.1

[56] References Cited

U.S. PATENT DOCUMENTS 3,833,620  9/1974  Saltzman ................. 260/397.1
3,969,503  7/1976  Saltzman ................. 260/397.1

*Primary Examiner*—Elbert L. Roberts
*Attorney, Agent, or Firm*—Bucknam and Archer

[57] ABSTRACT

Novel compounds are described, which are 7-acyl-chenodeoxycholic acid of formula (I)

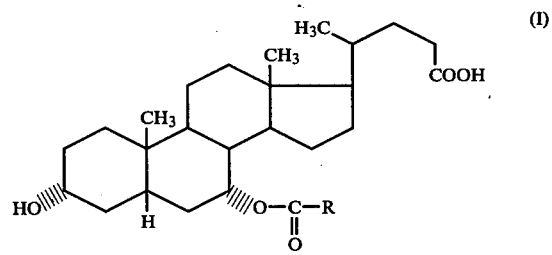

in which R-CO is the residue from a linear, saturated or unsaturated carboxylic acid of 3–18 carbon atoms or the residue from a cycloalkanecarboxylic acid of 3–7 carbon atoms in the cycloalkane ring. The compounds are prepared by selective hydrolysis of the 3,7-diacyl derivatives of chenodeoxycholic acid. The compounds are valuable against biliary calculosis, diskinesia and hypertriglyceridemia.

1 Claim, No Drawings

DERIVATIVES OF CHENODEOXYCHOLIC ACID

The present invention relates to novel derivatives of chenodeoxycholic acid and more specifically to 7-acyl-chenodeoxycholic acid of formula (I):

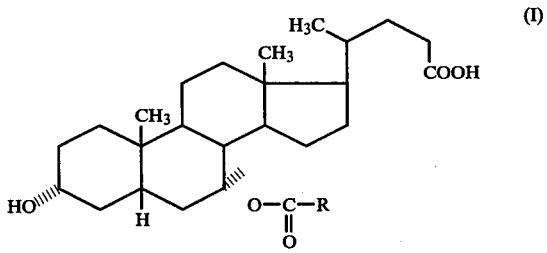

in which RCO is the residue of a linear carboxylic acid, which may be saturated or unsaturated, containing 3-18 carbon atoms or the residue from a cycloalkanecarboxylic acid containing 3-7 carbon atoms in the cycloalkane ring.

In particular, the group RCO may represent the acyl residue from acetic acid, butyric acid, caprylic acid, lauric acid, palmitic acid, stearic acid, oleic acid, linoleic acid, arachidonic acid, cyclopropancarboxylic acid, cyclobutancarboxylic acid, cyclopentancarboxylic acid, and cyclohexanecarboxylic acid.

The therapy with chenodeoxycholic acid in the field of biliary calculosis is well-established, (Coyen, et al, New England Journal of Medicine, 292, 604, 1975). Chenodeoxycholic acid enriches biliary acids of cholecystic bile, diminishes progressively the lithogenesis and may cause dissolution biliary calculi enriched in cholesterol. More recently, the use of chenodeoxycholic acid has been suggested also in the treatment of biliary diskinesia and hypertriglyceridemia, (Angelin, et al, J. Lipid Res. 19, 1017, 1978).

The action of antilithiasis of chenodeoxycholic acid against the formation of biliary calculi is limited in humans, however, due to its collateral side effects of subjective nature, such as nausea and diarrhea and also due to the metabolism itself of the biliary acid, which undergoes either 7-α-dehydroxylation or an oxidation to an inactive 7-ketoderivative compound. This oxidation, which occurss at the intestinal level, occurs under the action of enzymatic products of bacterial origin, (Ferrari, et al, FEBS Lett. 75, 176, 1977) and blocks the enterohepatic circuit of chenodeoxycolic acid so that inactive products result and the therapeutic efficacy of the antilithiasis agent is limited. It is also suspected that the formation of metabolites of chenodeoxycholic acid may lead to products having direct toxicity on the intestine as it has been demonstrated on the basis of several experimental researches, (Sauer, et al, Zschr. Gastroenterol., 17, 236, 1979).

It is, therefore, very important to achieve long lasting therapy of biliary calculosis and to provide derivatives which permit a continuous recycling of chenodeoxycholic acid and which diminish the possibility of inactivation at the intestinal level.

It has now been found that the 7-acylderivatives of formula (I), which will be referred to hereinbelow with the symbol CDC-7-esters, resist this inactivation in an unforeseeable manner, thus permitting a significant reduction in the daily doses and/or a significant increase in the intervals between each administration. The acyl derivatives of formula (I) have been found to be essentially devoid of toxicity in animals and in the course of experiments with experimental calculosis, they have shown antilithiasis activity, which is particularly in certain respects, substantially superior to that of chenodeoxycholic acid. Further, the esters of formula (I), CDC-7-esters, have demonstrated to possess an interesting hypotriglyceridemizing activity.

It is, therefore, another object of the present invention to provide pharmaceutical compositions for the therapy of biliary calculosis, biliary diskinesia and hypertriglyceridemia, which contain one or more CDC-7-esters of formula (I) as the active components.

A further object of the invention resides in the use of compounds of formula (I) for the therapy of biliary calculosis, biliary diskinesia and hypertriglyceridemia. The term "use" within the scope of the present invention, means all the operations which are inherent to the preparation of the compounds of this invention, including their purification, their formulation in pharmaceutical forms suitable for administration and/or the packaging in containers suitable for their administration.

Finally, the present invention relates to a process for the preparation of the CDC-7-esters of formula (I), which consists of selectively hydrolyzing under alkaline conditions, compounds of formula (II), that is 3,7-diacylderivatives of the methyl ester of chenodeoxycholic acid as illustrated in the reaction scheme reported hereinbelow,

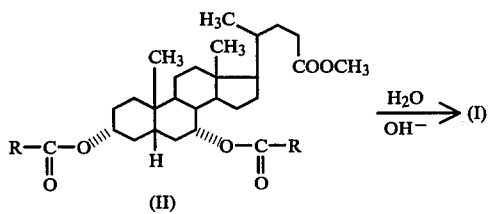

in which R-CO has the same meaning indicated hereinabove.

The selective hydrolysis shown in the reaction scheme hereinabove is carried out with sodium or potassium hydroxide in a solvent consisting of mixtures of lower alcohols with water or methylcellosolve with water or analogous mixtures.

For the preparation of the compounds of the present invention, the compounds of formula (II), the 3,7-diacylderivatives, may be prepared by acylation of the methyl ester of chenodeoxycholic acid with active derivatives of an acid of formula R-COOH, such as the acid chloride or anhydrides, including mixed anhydrides, suitably in the presence of a substance which acts as acid acceptor. A suitable procedure for the diacylation, which is particularly simple and which is accompanied by good yields, consists of reacting methyl chenodeoxycholate with an acyl chloride or anhydride in pyridine.

After the selective hydrolysis illustrated hereinabove, the compounds of formula (I), CDC-7-esters of formula (I), are isolated and purified by crystallization or when they are liquid at room temperature by chromatography in a column conveniently using silica.

The examples which follow illustrate the process of the present invention.

EXAMPLE 1

7-butyryl-chenodeoxycholic acid (formula I in which R is equal to n-propyl)

(a) A solution of 1 millimole of methyl chenodeoxycholate in 1.42 cc of pyridine is reacted with 9.8 millimoles of butyric anhydride. The mixture is warmed under reflux for three hours, then it is poured under agitation into ice and is acidified to a pH of 1 with 1:1 HCl. The precipitate is extracted with $CH_2Cl_2$; the organic solution is washed with a saturated solution of $NaHCO_3$ and then with water up to neutrality. The solution is dried over $Na_2SO_4$ and is then evaporated under vacuum up to constant weight. The product thus obtained consisting of 3,7-dibutyrylchenodeoxycholic acid methyl ester, is used without further purification for the subsequent reaction.

(b) A solution of 1 millimole of the diacylderivative, obtained according to (a) in 4.46 cc of methanol is added to 2.23 cc of water and 0.23 cc of KOH in an aqueous solution of 50% concentration. The material is heated to boiling in an inert atmosphere up to the point when chromatographic examination indicates that hydrolysis has occured, (60–90 minutes); the methanol is then evaporated under vacuum, the residue is acidified to a pH of 2 with 1:1 HCl and is then extracted with methylene chloride. The extract is dried over $Na_2SO_4$ and is then evaporated to dryness. The desired product is obtained pure by recrystallization from methanol. m.p. 192°–194° C., (the analytical data are reported in Table 1).

EXAMPLE 2

7-palmitoyl-chenodeoxycholic acid, (formula I in which R is equal to $CH_3—(CH_2)_{14}—$)

(a) A solution of 1 millimole of the methyl ester of chenodeoxycholic acid in 2 cc of pyridine is reacted with 2.5 millimoles of palmitoyl chloride. The mixture is heated under reflux for one hour, it is then poured into ice, and acidified with 1:1 HCl to a pH of 1. The product, 3,7-dipalmitoylchenodeoxycholic methyl ester is isolated as described in Example 1(a).

(b) The crude product obtained hereinabove is reacted with potassium hydroxide in aqueous methanol according to the procedure described in Example 1(b). The oil thus obtained at the end of the operation is chromatographed on a silica column in the ratio of 1:20 using as the eluent, mixtures of hexane and ethyl acetate in a ratio of increasing polarity from 9:1 to 6:4.

Table 1 summarizes some characteristic properties of the compounds of formula (I), CDC-7-esters obtained in accordance with the process of the present invention.

TABLE 1

| COMPOUND | M.P. °C. | Solvent of Recrystallization | FORMULA | ANALYSIS Calcd % | Found |
|---|---|---|---|---|---|
| CDC-7-butyrate | 192–94 | methanol | $C_{28}H_{46}O_5$ | C 72.73 | 73.01 |
| | | | | H 9.96 | 10.22 |
| CDC-7-cyclopropancarboxylate | 173–75 | methanol/water | $C_{28}H_{44}O_5$ | C 73.04 | 72.87 |
| | | | | H 9.57 | 9.48 |
| CDC-7-caprylate | 133–35 | methanol/water | $C_{32}H_{54}O_5$ | C 74.13 | 73.89 |
| | | | | H 10.42 | 10.61 |
| CDC-7-laurate | 97–99 | diethylether/hexane | $C_{36}H_{62}O_5$ | C 75.26 | 75.09 |
| | | | | H 10.80 | 10.96 |
| CDC-7-palmitate | oil | — | $C_{40}H_{70}O_5$ | C 76.19 | 76.37 |
| | | | | H 11.11 | 10.97 |
| CDC-7-oleate | oil | — | $C_{42}H_{72}O_5$ | C 76.83 | 77.00 |
| | | | | H 10.98 | 11.05 |
| CDC-7-linoleate | oil | — | $C_{42}H_{70}O_5$ | C 77.06 | 77.02 |
| | | | | H 10.70 | 10.90 |

The CDC-7-esters reported hereinabove by NMR analysis (in $CDCl_3$, internal reference TMS) give the following characteristic data:

3.15/3.27—3.80/4.00 (1H, m, >CHOH);
4.70/4.85—5.00/5.90 (1H, m, >CH—O—OC—R);
5.90/6.65—6.30/7.10 (2H, m, —COOH, —OH).

In addition the oleate and linoleate give signals at 5.27–5.60 (2H, m, CH=CH) and at 5.05–5.75 (4H, 2CH=CH), respectively.

On infrared analysis, all the compounds of formula I give absorption at 3540 and 3420 $cm^{-1}$ (OH), and at 1720 $cm^{-1}$ (enlarged band, COOH, O—OC—R).

The biological activity of the compounds of the present invention has been tested on the model of biliary calculosis with Syrian Cricetidae. In this model, (Dam and Christensen, Acta Path. Microbiol. Scand. 30, 236, 1952), the animals are exposed to a semi-purified diet, which contains 74.3% saccharose, 20% casein, 5% of a mixture of salts, 0.5% of a vitamin mixture and 0.2% of choline chloride. The food, as well as chenodeoxycholic acid and its derivatives, are administered for a period of 53 days. At the end of the treatment, the animals are sacrificed and the bile is classified as clear or opaque. Obviously, the animals, which have biliary calculi are counted.

The results reported in Table 2 show that chenodeoxycholic acid administered in the amount of 0.2% of the food, does not give any significant effect either on the properties of the bile or on the incidence of calculosis. However, it exhibits a very small toxicity, which has reduced the number of surviving animals (19 over 25). The derivatives with relatively short chain substituents such as the acetate, laurate and butyrate, reduce the number of biliary calculi, but in a manner, which is not statistically significant. The derivatives with an unsaturated long chain substituent, (oleate and linoleate), maintain a clear bile in the great majority of the animals and may totally prevent the occurrence of calculosis.

TABLE 2

Incidence of Calculosis in Cricetidae Treated with a Lithogenic Diet which Produces Calculi (group of 25 animals treated for 53 days)

| | % of diet | Clear Bile | Opaque Bile | Calculi |
|---|---|---|---|---|
| Controls | — | 8/25 (32%) | 7/25 (28%) | 10/25 (40%) |
| Chenodeoxycholic Acid (CDC) | 0.200 | 5/19 (26%) | 6/19 (32%) | 8/19 (42%) |
| CDC-7-acetate(*) | 0.214 | 9/20 (45%) | 5/20 (25%) | 6/20 (30%) |
| CDC-7-laurate | 0.293 | 7/22 (32%) | 7/22 (32%) | 8/22 (36%) |
| CDC-7-butyrate | 0.236 | 3/24 (13%) | 15/24 (63%) | 6/24 (25%) |
| CDC-7-oleate | 0.335 | 16/25 (64%) | 9/25 (36%) | 0/25 (0%) |
| CDC-7-linoleate | 0.336 | 16/24 (67%) | 8/24 (33%) | 0/24 (0%) |

(*)E. Hanser, E. Baumgartner, K. Meyer, Helvetica Chimica Acta.

The experimental toxicity of the compounds has been tested in Swiss mice of average weight 25–30 grams in the case of the male mice and 20–25 grams in the case of the female mice. For the determination of the toxicity, the compounds have been administered in doses of between 10 mg per kg and 2,000 mg per kg suspended in carboxymethylcellulose so as to administer 0.5 cc of suspension to a mouse of 20 grams weight. After individual administrations of each compound, the animals have been followed for a period of ten days. All the compounds tested, that is chenodeoxycholic acid, (CDC), CDC-7-acetate, CDC-7-laurate, CDC-7-butyrate, CDC-7-oleate, and CDC-7-linoleate have not caused any death in the test described hereinabove so that the $DL_{50}$ must be considered superior to 2,000 mg/kg. During the experiment of determination of acute toxicity, the animals have not manifested any clear sign of toxicity.

It is concluded, therefore, that the esters in the 7 position of chenodeoxycholic acid with fatty acids having a long unsaturated chain, do not manifest any acute toxicity in the laboratory animals and are exceptionally active in the experimental calculosis of cricetidae while chenodeoxycholic acid is practically inactive in the equivalent amounts.

The compound of formula (I) may be administered to patients affected by biliary calculosis, biliary diskinesia or hypertriglyceridemia in doses of 50–500 mg administration 1–4 times daily. The forms of administrations are the same as commonly used in pharmaceutical formulations; particularly suitable are the capsules Scherer.

The conventional inert pharmaceutically compatible excipients may be incorporated in the pharmaceutical compositions according to the present invention.

What is claimed is:

1. The compound 7-oleyl chenodeoxycholic acid.

* * * * *